US012569189B2

(12) United States Patent
Choe

(10) Patent No.: US 12,569,189 B2
(45) Date of Patent: Mar. 10, 2026

(54) DEVICE, METHOD AND COMPUTER PROGRAM FOR DETERMINING SLEEP EVENT USING RADAR

(71) Applicant: BITSENSING INC., Seongnam-si (KR)

(72) Inventor: Sun Taag Choe, Seoul (KR)

(73) Assignee: BITSENSING INC., Seongnam-si (KR)

( * ) Notice: Subject to any disclaimer, the term of this patent is extended or adjusted under 35 U.S.C. 154(b) by 172 days.

(21) Appl. No.: 18/119,596

(22) Filed: Mar. 9, 2023

(65) Prior Publication Data

US 2023/0284972 A1 Sep. 14, 2023

(30) Foreign Application Priority Data

Feb. 15, 2023 (KR) ........................ 10-2023-0020009

(51) Int. Cl.
| | |
|---|---|
| *A61B 5/00* | (2006.01) |
| *A61B 5/05* | (2021.01) |
| *G01S 7/41* | (2006.01) |

(52) U.S. Cl.
CPC .............. *A61B 5/4818* (2013.01); *A61B 5/05* (2013.01); *A61B 5/7267* (2013.01);
(Continued)

(58) Field of Classification Search
CPC ....... A61B 5/4818; A61B 5/05; A61B 5/7267; A61B 5/7275; A61B 5/7278;
(Continued)

(56) References Cited

U.S. PATENT DOCUMENTS

| | | | | |
|---|---|---|---|---|
| 2013/0053653 A1* | 2/2013 | Cuddihy | .............. | A61B 5/0816 |
| | | | | 600/301 |
| 2021/0398666 A1* | 12/2021 | Maslik | ................. | A61B 5/4842 |

FOREIGN PATENT DOCUMENTS

| | | | |
|---|---|---|---|
| CN | 110710963 A | | 1/2020 |
| JP | 2014210137 A | * | 11/2014 |

(Continued)

OTHER PUBLICATIONS

Extended European Search Report for EP application No. 23161133.6 dated Jul. 19, 2023.

*Primary Examiner* — Michael J Carey
*Assistant Examiner* — Zainab Mohammed Aldarraji
(74) *Attorney, Agent, or Firm* — Dinsmore & Shohl LLP; Yongsok Choi, Esq.

(57) ABSTRACT

A device for determination of a sleep event using a radar includes a transceiver configured to transmit a radar signal toward a subject and receives the radar signal reflected from the subject; an average breathing signal derivation unit configured to derive an average breathing signal of the subject based on the radar signal; a breathing feature information generation unit configured to compare the radar signal with the average breathing signal and generate breathing feature information of the subject; a prediction information derivation unit configured to derive event occurrence prediction information for a plurality of sleep items based on the breathing feature information; and a sleep event determination unit configured to determine whether a sleep event has occurred in the subject based on the event occurrence prediction information.

13 Claims, 11 Drawing Sheets

1

(52) U.S. Cl.
CPC .......... *A61B 5/7275* (2013.01); *A61B 5/7278*
(2013.01); *G01S 7/415* (2013.01)

(58) Field of Classification Search
CPC ..... A61B 5/1113; A61B 5/0816; A61B 5/113;
A61B 5/726; A61B 5/7282; A61B
5/0507; A61B 5/7264; G01S 7/415;
G16H 40/63; G16H 20/70; G16H 50/20;
G16H 50/30
See application file for complete search history.

(56) References Cited

FOREIGN PATENT DOCUMENTS

| | | | | | |
|---|---|---|---|---|---|
| JP | 6353194 | B2 | 7/2018 | | |
| KR | 10-2018-0077453 | A | 7/2018 | | |
| KR | 10-2321991 | B1 | 11/2021 | | |
| WO | WO-2021046342 | A1 * | 3/2021 | .......... | A61B 5/0205 |
| WO | 2022026623 | A1 | 2/2022 | | |

* cited by examiner $$b[i] = \frac{F}{L} \sum_{j=0}^{L-1} x[i-j]$$

<Baseline Signal>     <Respiration Signal>

DEVICE, METHOD AND COMPUTER PROGRAM FOR DETERMINING SLEEP EVENT USING RADAR

CROSS-REFERENCE TO RELATED APPLICATION

This application claims the benefit under 35 USC 119(a) of Korean Patent Applications No. 10-2022-0030032 filed on Mar. 10, 2022, and No. 10-2023-0020009 filed on Feb. 15, 2023 in the Korean Intellectual Property Office, the entire disclosures of which are incorporated herein by reference for all purposes.

TECHNICAL FIELD

The present disclosure relates to a device, a method and a computer program for determination of a sleep event using a radar.

BACKGROUND

Polysomnography is a test used to measure the quality and amount of sleep and detect sleep diseases and sleep-related disorders. In general, polysomnography is used to detect a variety of sleep disorders by measuring physiological and physical signals from human body during sleep. For example, brain waves, electrooculogram, electromyogram, electrocardiogram, arterial blood, oxygen saturation, abdominal and thoracic breathing exercises, respiratory air flow, snoring and body postures are measured.

A basic method for measuring the quality and amount of sleep uses a wrist actigraphy device to measure sleep time. Specifically, sleep time of a wearer wearing a wrist actigraphy device is measured and tossing or the like during sleep is detected based on activities of the wearer.

Also, a photoplethysmography (PPG) device worn on the wrist is used to measure the heart rate and heart rate variability of the wearer during sleep. Specifically, sleep stages of the wearer are distinguished, and oxygen desaturation caused by apnea is detected by measuring oxygen saturation ($SpO_2$).

However, the conventional test method can predict the quality of sleep (for example, satisfaction caused by tiredness), but cannot distinguish between obstructive sleep apnea (OSA) and central sleep apnea (CSA) that cause apnea.

Specifically, sleep apnea is divided into OSA that is a repetitive breathing cessation during sleep due to obstruction of upper airway and CSA that is a pause in breathing during sleep without giving effort to breathe. OSA is a representative symptom of sleep disorder, accounting for about 90% of sleep apnea cases, and CSA is observed only in some cases.

The conventional test method needs to be performed while a tester is worn on a part of a human body, and depends only on an expensive tester to more precisely examine sleep diseases.

PRIOR ART DOCUMENT (Patent Document 1) Korean Patent Publication No. 10-2321991 (registered on Oct. 29, 2021)
(Patent Document 2) Korean Patent Laid-open Publication No. 10-2018-0077453 (published on Jul. 9, 2018)

SUMMARY

In view of the foregoing, the present disclosure provides a device, a method and a computer program for determination of a sleep event that can classify breathing patterns of a human during sleep and can also detect a sleep breathing disorder and an occurrence time of the sleep breathing disorder during sleep by using a radar.

The problems to be solved by the present disclosure are not limited to the above-described problems. There may be other problems to be solved by the present disclosure.

According to an exemplary embodiment, a device for determination of a sleep event using a radar may include a transceiver configured to transmit a radar signal toward a subject and receives the radar signal reflected from the subject; an average breathing signal derivation unit configured to derive an average breathing signal of the subject based on the radar signal; a breathing feature information generation unit configured to compare the radar signal with the average breathing signal and generate breathing feature information of the subject; a prediction information derivation unit configured to derive event occurrence prediction information for a plurality of sleep items based on the breathing feature information; and a sleep event determination unit configured to determine whether a sleep event has occurred in the subject based on the event occurrence prediction information.

According to another exemplary embodiment, a method for determination of a sleep event using a radar may include transmitting a radar signal toward a subject; receiving the radar signal reflected from the subject; deriving an average breathing signal of the subject based on the radar signal; comparing the radar signal with the average breathing signal and generating breathing feature information of the subject; deriving event occurrence prediction information for a plurality of sleep items based on the breathing feature information; and determining whether a sleep event has occurred in the subject based on the event occurrence prediction information.

According to another exemplary embodiment, a non-transitory computer-readable storage medium that stores a sequence of instructions for determination of a sleep event using a radar, wherein the sequence of instructions, when executed by a computing device, causes a computing device to: transmit a radar signal toward a subject; receive the radar signal reflected from the subject; derive an average breathing signal of the subject based on the radar signal; compare the radar signal with the average breathing signal and generate breathing feature information of the subject; derive event occurrence prediction information for a plurality of sleep items based on the breathing feature information; and determine whether a sleep event has occurred in the subject based on the event occurrence prediction information.

This summary is provided by way of illustration only and should not be construed as limiting in any manner. Besides the above-described exemplary embodiments, there may be additional exemplary embodiments that become apparent by reference to the drawings and the detailed description that follows.

According to any one of the above-described embodiments of the present disclosure, it is possible to analyze sleep-related breathing signals during sleep of a human by using a radar and thus possible to calculate the number of arousals caused by breathing disorders during sleep. It is possible to detect a sleep disorder and an occurrence time of the sleep disorder and determine a sleep-related disease by using the breathing signals of the human.

Also, the radar may be used to determine sleep-related symptoms including OSA, CSA and mixed sleep apnea. That is, it is possible to precisely determine sleep-related symptoms of the human and analyze the causes thereof as in polysomnography without performing polysomnography.

Further, the radar can be used to easily analyze sleep breathing of the human in daily life. Therefore, it is possible to provide a device, a method and a computer program for determination of a sleep event that can continuously monitor sleep-related symptoms and can be easily used in a contactless manner.

BRIEF DESCRIPTION OF THE DRAWINGS

In the detailed description that follows, embodiments are described as illustrations only since various changes and modifications will become apparent to a person with ordinary skill in the art from the following detailed description. The use of the same reference numbers in different figures indicates similar or identical items.

FIG. 8 is a diagram for explaining a sleep event occurrence session.

FIG. 9 is a diagram for explaining determining whether a sleep event has occurred.

DETAILED DESCRIPTION

Figure 1:
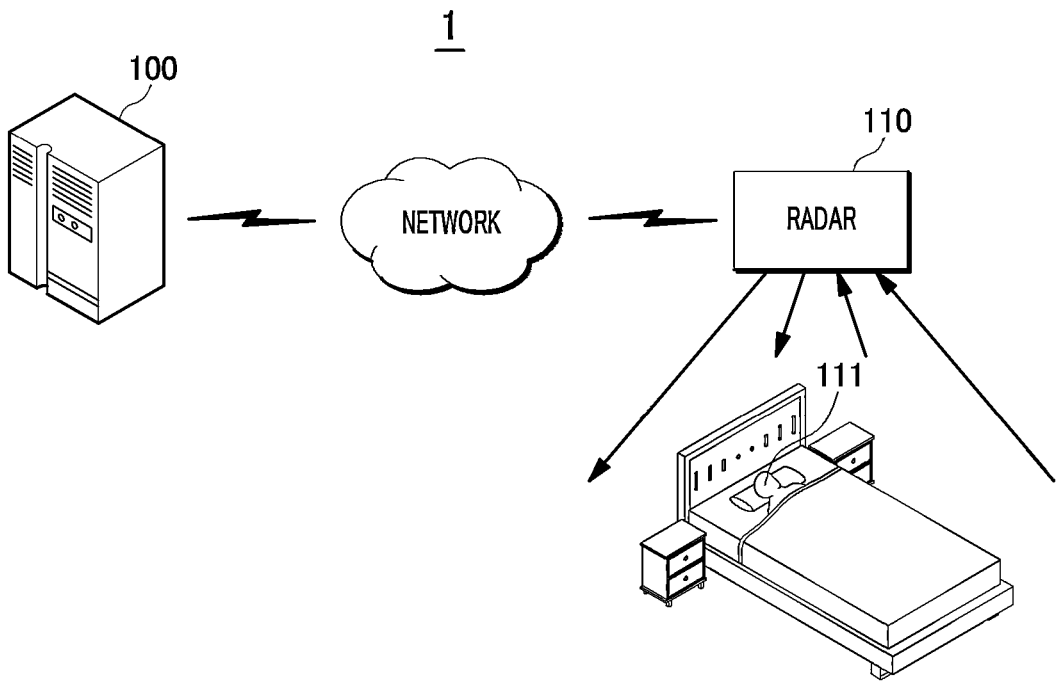
FIG. 1 is a configuration diagram of a sleep event determination system.

Hereafter, example embodiments will be described in detail with reference to the accompanying drawings so that the present disclosure may be readily implemented by those skilled in the art. However, it is to be noted that the present disclosure is not limited to the example embodiments but can be embodied in various other ways. In the drawings, parts irrelevant to the description are omitted for the simplicity of explanation, and like reference numerals denote like parts through the whole document.

Throughout this document, the term "connected to" may be used to designate a connection or coupling of one element to another element and includes both an element being "directly connected" another element and an element being "electronically connected" to another element via another element. Further, it is to be understood that the terms "comprises," "includes," "comprising," and/or "including" means that one or more other components, steps, operations, and/or elements are not excluded from the described and recited systems, devices, apparatuses, and methods unless context dictates otherwise; and is not intended to preclude the possibility that one or more other components, steps, operations, parts, or combinations thereof may exist or may be added. Throughout this document, when a member is said to be located "on" another member, this includes not only when the member is in contact with another member, but also when other member is present between the two members.

Throughout this document, the term "unit" may refer to a unit implemented by hardware, software, and/or a combination thereof. As examples only, one unit may be implemented by two or more pieces of hardware or two or more units may be implemented by one piece of hardware.

Throughout this document, a part of an operation or function described as being carried out by a terminal or device may be implemented or executed by a device connected to the terminal or device. Likewise, a part of an operation or function described as being implemented or executed by a device may be so implemented or executed by a terminal or device connected to the device.

Hereinafter, embodiments of the present disclosure will be explained in detail with reference to the accompanying drawings.

FIG. 1 is a configuration diagram of a sleep event determination system. Referring to FIG. 1, a sleep event determination system 1 may include a sleep event determination device 100 and a radar 110.

The components of the sleep event determination system 1 illustrated in FIG. 1 are typically connected to each other via a network. For example, as illustrated in FIG. 1, the sleep event determination device 100 and the radar 110 may be connected simultaneously or sequentially.

The sleep event determination device 100 may analyze breathing signals of a subject 111 by using the radar 110 during sleep of the subject 111. The sleep event determination device 100 may detect a sleep disorder and an occurrence time of the sleep disorder and determine a sleep-related disease by using the breathing signals of the subject 111.

For example, the sleep event determination device 100 is arranged to keep a predetermined distance from the subject 111 in sleep, and may transmit a radar signal toward the subject 111 and receive the radar signal reflected from the subject 111 by using the radar 110.

The sleep event determination device 100 may determine sleep-related symptoms, such as OSA, CSA and mixed sleep apnea, of the subject 111 by using the radar 110.

Therefore, the sleep event determination device 100 can precisely determine sleep-related symptoms of the subject 111 and analyze the causes as in polysomnography without performing polysomnography.

Since the sleep event determination device 100 analyzes the breathing signals related to the sleep of the subject 111 by using the radar 110, it is possible to reduce inconvenience incurred in performing polysomnography. Also, the sleep event determination device 100 can easily analyze sleep breathing of the subject 111 in daily life and continuously monitor sleep-related symptoms. Further, the sleep event determination device 100 can analyze sleep breathing of the subject 111 in a contactless manner.

Hereafter, each component of the sleep event determination device 100 will be described.

Figure 2:
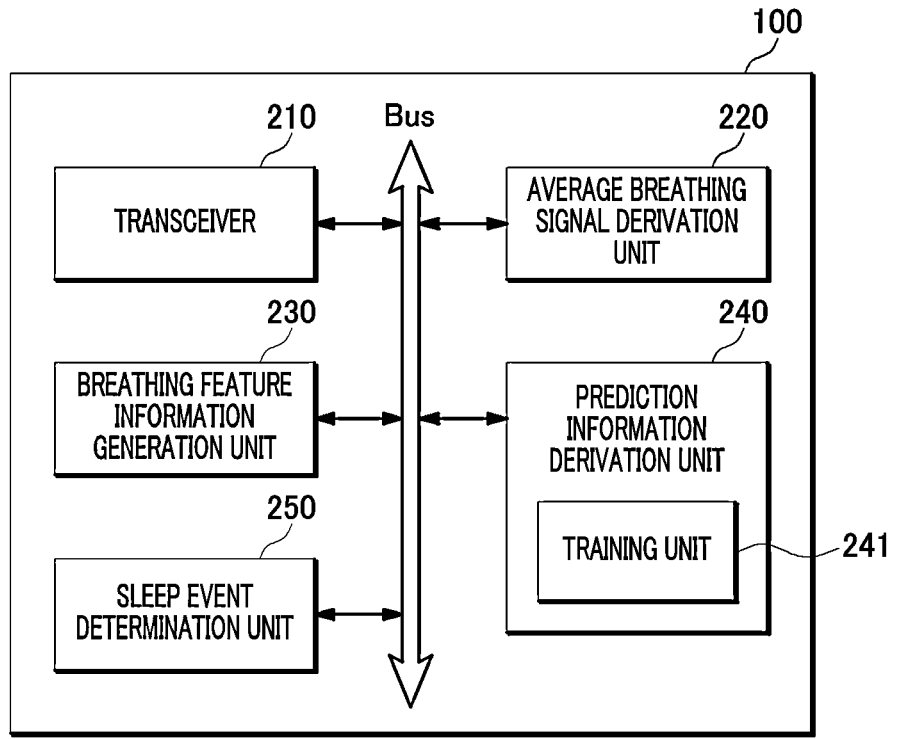
FIG. 2 is a configuration diagram of a sleep event determination device.

FIG. 2 is a configuration diagram of the sleep event determination device. Referring to FIG. 2, the sleep event determination device 100 may include a transceiver 210, an average breathing signal derivation unit 220, a breathing feature information generation unit 230, a prediction information derivation unit 240 and a sleep event determination unit 250. Also, the prediction information derivation unit 240 may include a training unit 241. However, these components 210 to 250 are just examples of components that can be controlled by the sleep event determination device 100.

The transceiver 210 may transmit a radar signal toward a subject. The transceiver 210 may receive the radar signal reflected from the subject. For example, the transceiver 210 may transmit a radar signal toward the subject and receive the radar signal reflected from the subject by using a radar.

The average breathing signal derivation unit 220 may derive an average breathing signal of a subject based on a radar signal. For example, the average breathing signal derivation unit 220 may calculate a signal corresponding to usual breathing of the subject by using a pattern of the radar signal reflected from the subject and a change in amplitude of the signal.

Specifically, the average breathing signal derivation unit 220 may derive an average breathing signal of the subject every predetermined unit time based on a time sensitivity factor and an amplitude sensitivity factor of the radar signal. Hereafter, deriving an average breathing signal will be described with reference to FIG. 3.

Figure 3:
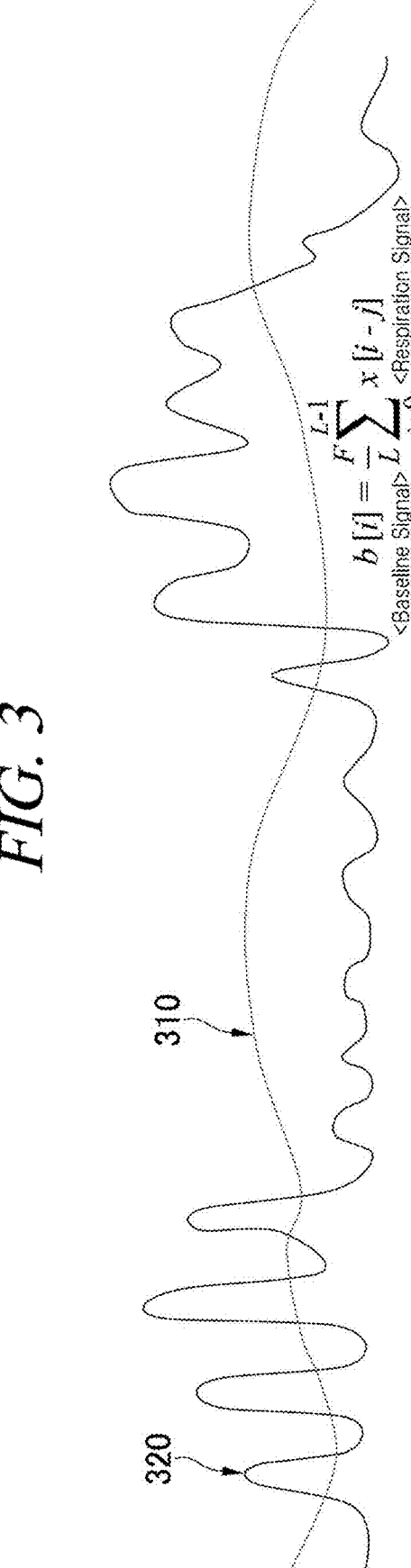
FIG. 3 is a diagram for explaining deriving an average breathing signal.

FIG. 3 is a diagram for explaining deriving an average breathing signal. Referring to FIG. 3, the average breathing signal derivation unit 220 may derive an average breathing signal 310 of the subject by using a radar signal 320 reflected from the subject. For example, the average breathing signal derivation unit 220 may derive the average breathing signal 310 by using a time sensitivity factor and an amplitude sensitivity factor based on the radar signal 320. The average breathing signal derivation unit 220 may use Equation 1 below.

$$b[i] = \frac{F}{L}\sum_{j=0}^{L-1}x[i-j] \qquad \text{<Equation 1>}$$

In Equation 1 (see FIG. 3), b is the average breathing signal 310 of the subject and x is the radar signal 320 reflected and received from the subject. Also, L is the time sensitivity factor that means the length of specific sequential time periods and is an integer obtained by multiplying the frequency of the radar signal in sequence by the length of time in second. Further, F is the amplitude sensitivity factor that responds to the amplitude of the specific sequential time periods.

Referring to Equation 1, the waveform of the average breathing signal of the subject may become obtuse over time as the time sensitivity factor increases and the amplitude sensitivity factor decreases, and may become sharp over time as the time sensitivity factor decreases and the amplitude sensitivity factor increases.

Figure 4:
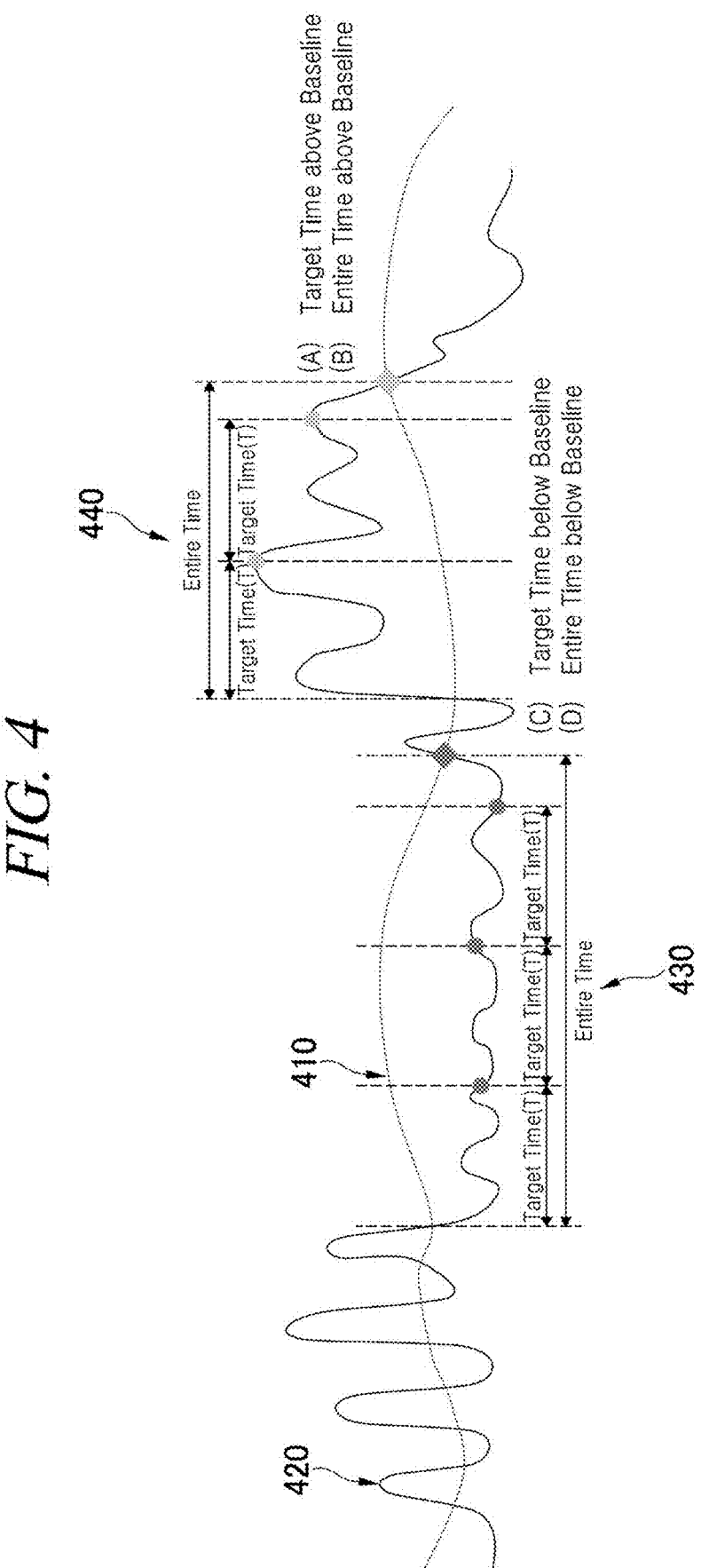
FIG. 4 is a diagram for explaining detecting a breathing feature session.

FIG. 4 is a diagram for explaining detecting a breathing feature session. Referring to FIG. 4, the breathing feature information generation unit 230 may generate breathing feature information of the subject by comparing an average breathing signal 410 and a radar signal 420.

The breathing feature information generation unit 230 may detect breathing feature sessions of the subject by detecting durations 430 and 440 in which the radar signal 420 strays from the average breathing signal 410 for a predetermined threshold time period or more.

For example, the breathing feature information generation unit 230 may compare the radar signal 420 received from the subject with the average breathing signal 410. For example, the breathing feature information generation unit 230 may detect the duration 430 in which the radar signal 420 is smaller than the average breathing signal 410. When the duration 430 in which the radar signal 420 is smaller than the average breathing signal 410 for a predetermined threshold time period T or more, the breathing feature information generation unit 230 may detect the duration 430 as a breathing feature session of the subject.

For another example, the breathing feature information generation unit 230 may detect the duration 440 in which the radar signal 420 is greater than the average breathing signal 410. When the duration 440 in which the radar signal 420 is greater than the average breathing signal 410 for the predetermined threshold time period T or more, the breathing feature information generation unit 230 may detect the duration 440 as a breathing feature session of the subject.

Figure 5A:
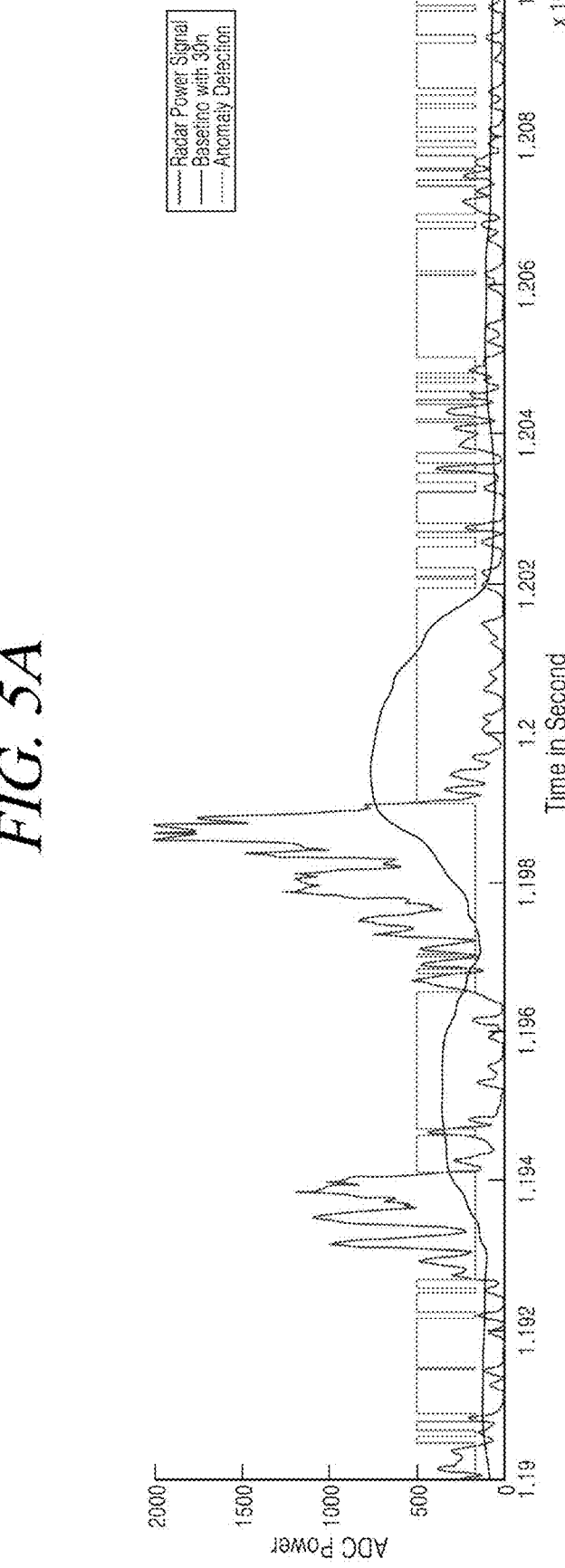
FIGS. 5A, 5B, and 5C are diagrams for explaining the detected breathing feature session.
Figure 5B:
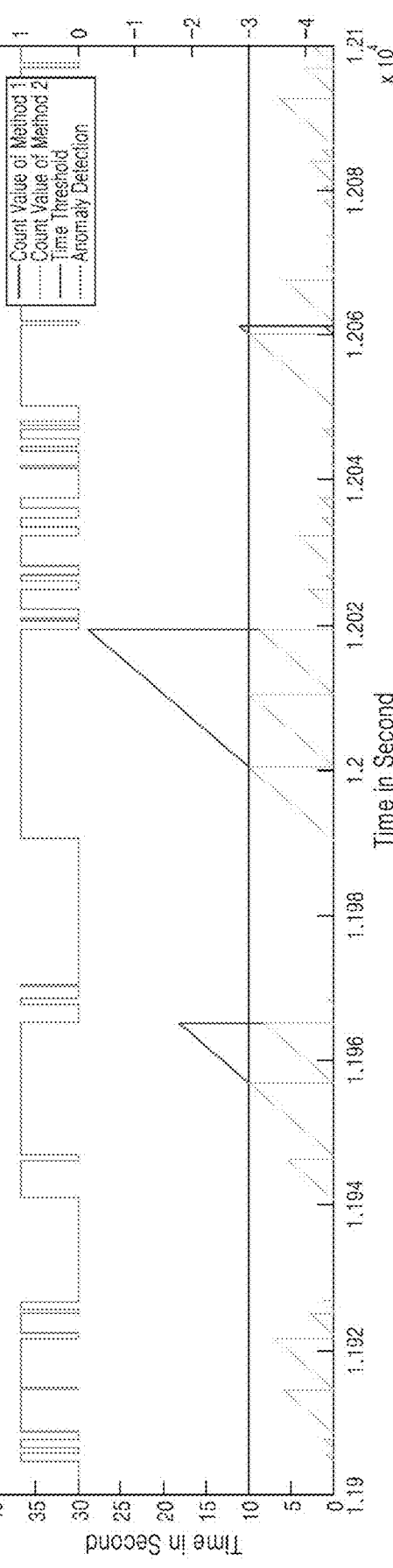
Figure 5C:
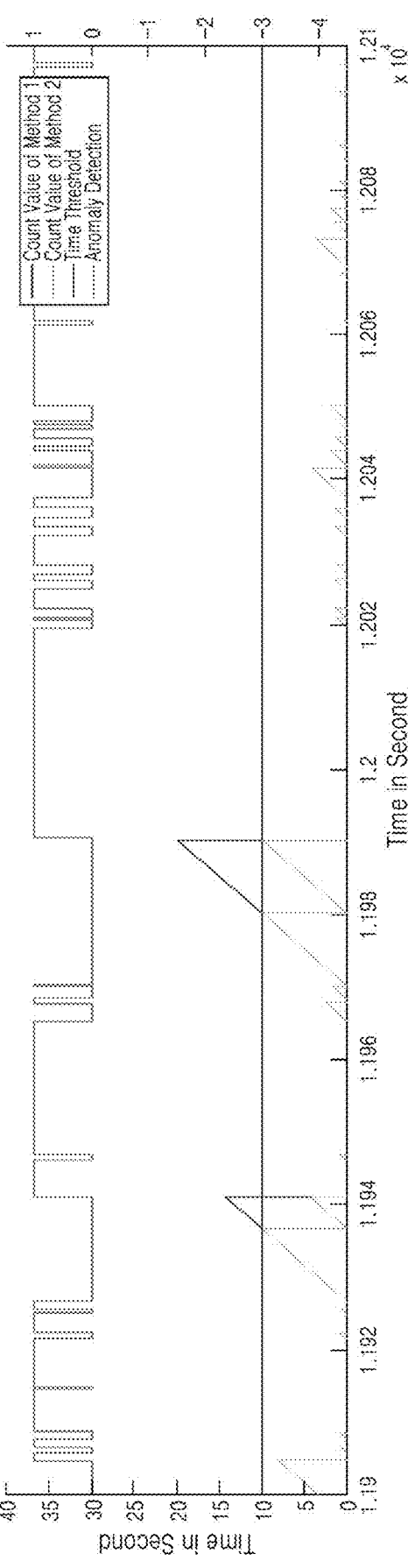

FIG. 5 is a diagram for explaining the detected breathing feature session. FIG. 5A shows the average breathing signal of the subject, and FIG. 5B and FIG. 5C show the subject's breathing feature sessions detected based on the radar signal received from the subject.

Specifically, FIG. 5B shows the subject's breathing feature session detected when the duration in which the radar signal received from the subject is smaller than the average breathing signal for a threshold time period or more, and FIG. 5C shows the subject's breathing feature session detected when the duration in which the radar signal received from the subject is greater than the average breathing signal for the threshold time period or more.

Figure 6:
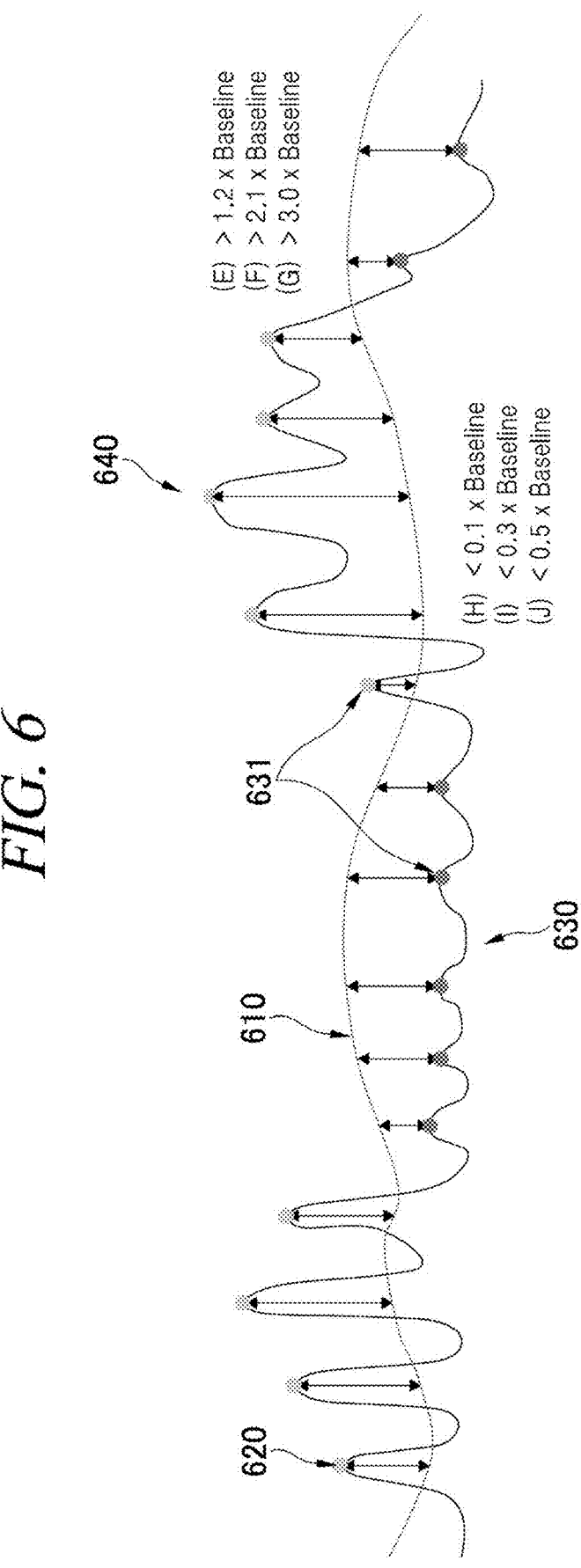
FIG. 6 is a diagram for explaining generating breathing feature information.

FIG. 6 is a diagram for explaining generating breathing feature information.

Referring to FIG. 6, the breathing feature information generation unit 230 may derive peaks 631 and 641 from the radar signal 620 in the breathing feature sessions 630 and 640, respectively.

The breathing feature information generation unit 230 may generate breathing feature information of the subject based on the peaks 631 and 641, an average breathing signal 610 and predetermined threshold conditions E, F, G, H, I and J. Herein, the predetermined threshold conditions (E, F, G, H, I and J in FIG. 6) may correspond to Equations 2 to 7 below.

$$[1.2\times\text{average breathing signal value}]<[\text{peak value}]\leq [2.1\times\text{average breathing signal value}] \qquad \text{<Equation 2>}$$

$$[2.1\times\text{average breathing signal value}]<[\text{peak value}] [3.0\times\text{average breathing signal value}] \qquad \text{<Equation 3>}$$

$$[3.0\times\text{average breathing signal value}]<[\text{peak value}] \qquad \text{<Equation 4>}$$

Equations 2, 3 and 4 may be the predetermined threshold conditions corresponding to E, F and G, respectively, shown in FIG. 6. For example, when the peak 641 of the radar signal 620 in the breathing feature session 640 satisfies Equations 2 to 4 as compared with the average breathing signal 610, the breathing feature information generation unit 230 may generate breathing feature information of the subject from the breathing feature session 640.

$$[\text{Peak value}]<[0.1\times\text{average breathing signal value}] \qquad \text{<Equation 5>}$$

$$[0.1\times\text{average breathing signal value}][\text{Peak value}]< [0.3\times\text{average breathing signal value}] \qquad \text{<Equation 6>}$$

$$[0.3\times\text{average breathing signal value}][\text{Peak value}]< [0.5\times\text{average breathing signal value}] \qquad \text{<Equation 7>}$$

Equations 5, 6 and 7 may be the predetermined threshold conditions corresponding to H, I and J, respectively, shown in FIG. 6. For example, when the peak 631 in the breathing feature session 630 satisfies Equations 5 to 7 as compared with the average breathing signal 610, the breathing feature information generation unit 230 may generate breathing feature information of the subject from the breathing feature session 630.

The prediction information derivation unit 240 may derive event occurrence prediction information for a plurality of sleep items based on the breathing feature information.

Specifically, the prediction information derivation unit 240 may include the training unit 241. The training unit 241 may train a prediction model based on label values for respective sleep events associated with the plurality of sleep items.

The prediction information derivation unit 240 may derive event occurrence prediction information using the prediction model. For example, the prediction information derivation unit 240 may derive an event occurrence prediction value by inputting the generated breathing feature information into the trained prediction model.

The sleep event determination unit 250 may determine whether a sleep event has occurred in the subject based on the event occurrence prediction information. For example, the sleep event determination unit 250 may determine whether the subject has a sleep disorder based on the event occurrence prediction value derived from the prediction model.

Specifically, the sleep event determination unit 250 may calculate a moving summation of the event occurrence prediction information. The sleep event determination unit 250 may derive a maximum likelihood value of the moving summation. The sleep event determination unit 250 may determine whether a sleep event has occurred in the subject based on the maximum likelihood value.

Figure 7:
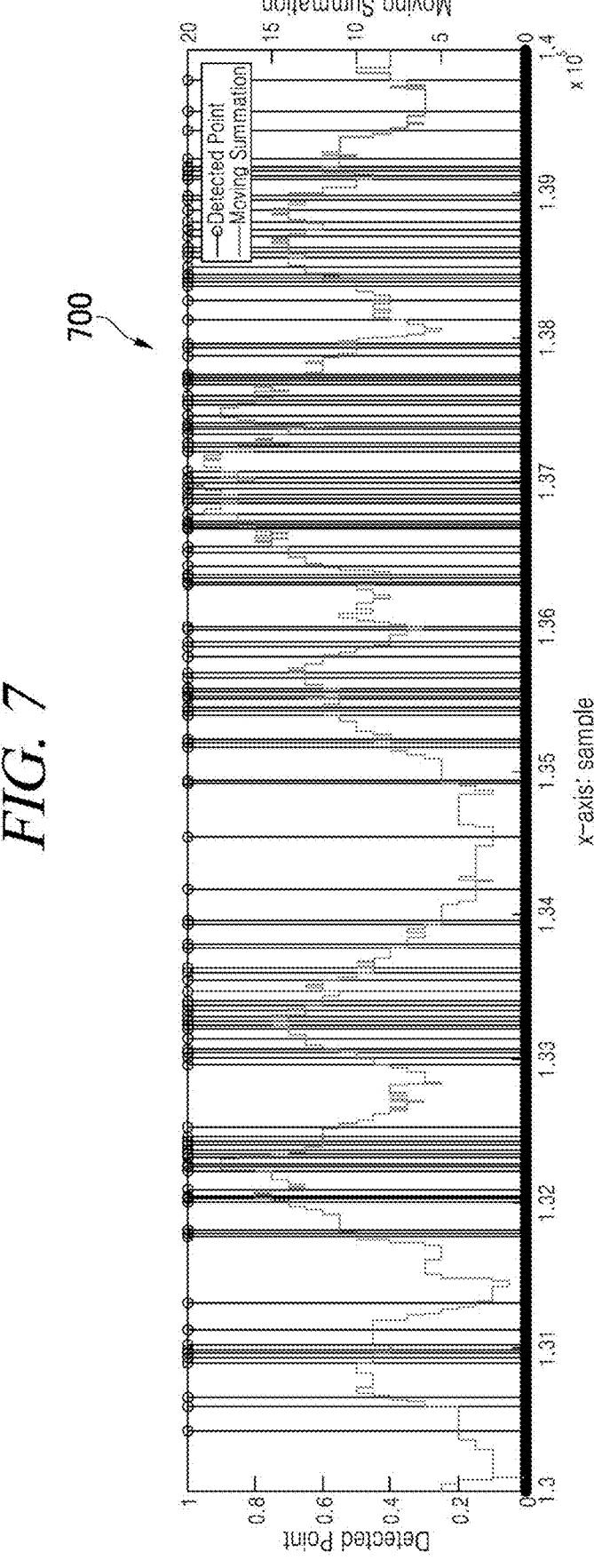
FIG. 7 is a diagram for explaining calculating a moving summation of event occurrence prediction information.

FIG. 7 is a diagram for explaining calculating a moving summation of event occurrence prediction information. Referring to a graph 700 of FIG. 7, the sleep event determination unit 250 may calculate a moving summation of each of sleep event occurrence prediction values derived from the prediction model. For example, the sleep event determination unit 250 may calculate a moving summation based on Equation 8 below. For example, the moving summation may have a window size of 60 seconds (600 samples).

$$y[i] = \sum_{j=0}^{60s} x[i-j] \qquad \text{<Equation 8>}$$

Figure 8:
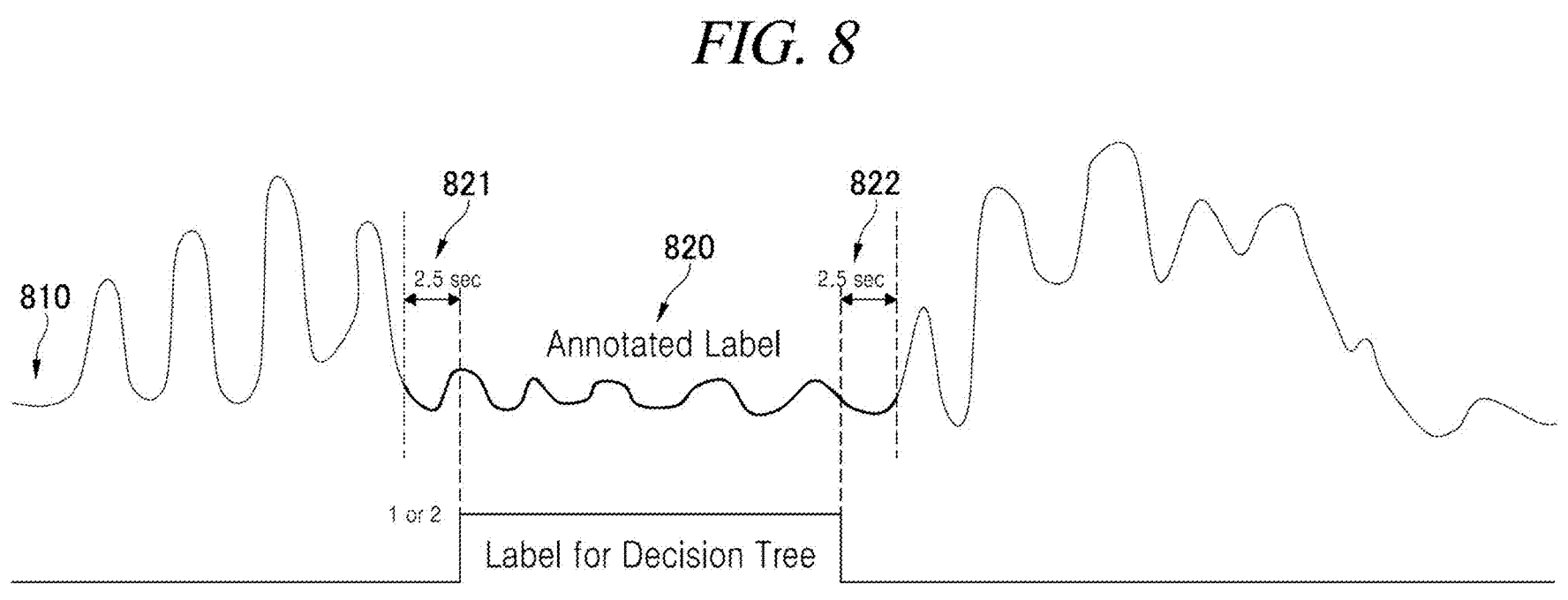

FIG. 8 is a diagram for explaining a sleep event occurrence session. Referring to FIG. 8, the sleep event determination unit 250 may set predetermined margin durations 821 and 822 respectively at a start point and an end point of the occurrence of a sleep event for a derived sleep event occurrence prediction value 820. The margin duration may refer to an avoidance duration in which confusion in learning may occur in a continuous signal.

For example, the sleep event determination unit 250 may set a start margin duration 821 of 2.5 seconds at a start point of the occurrence of a sleep event in a radar signal 810 and an end margin duration 822 of 2.5 seconds at an end point of the occurrence of the sleep event in the radar signal 810.

Figure 9:
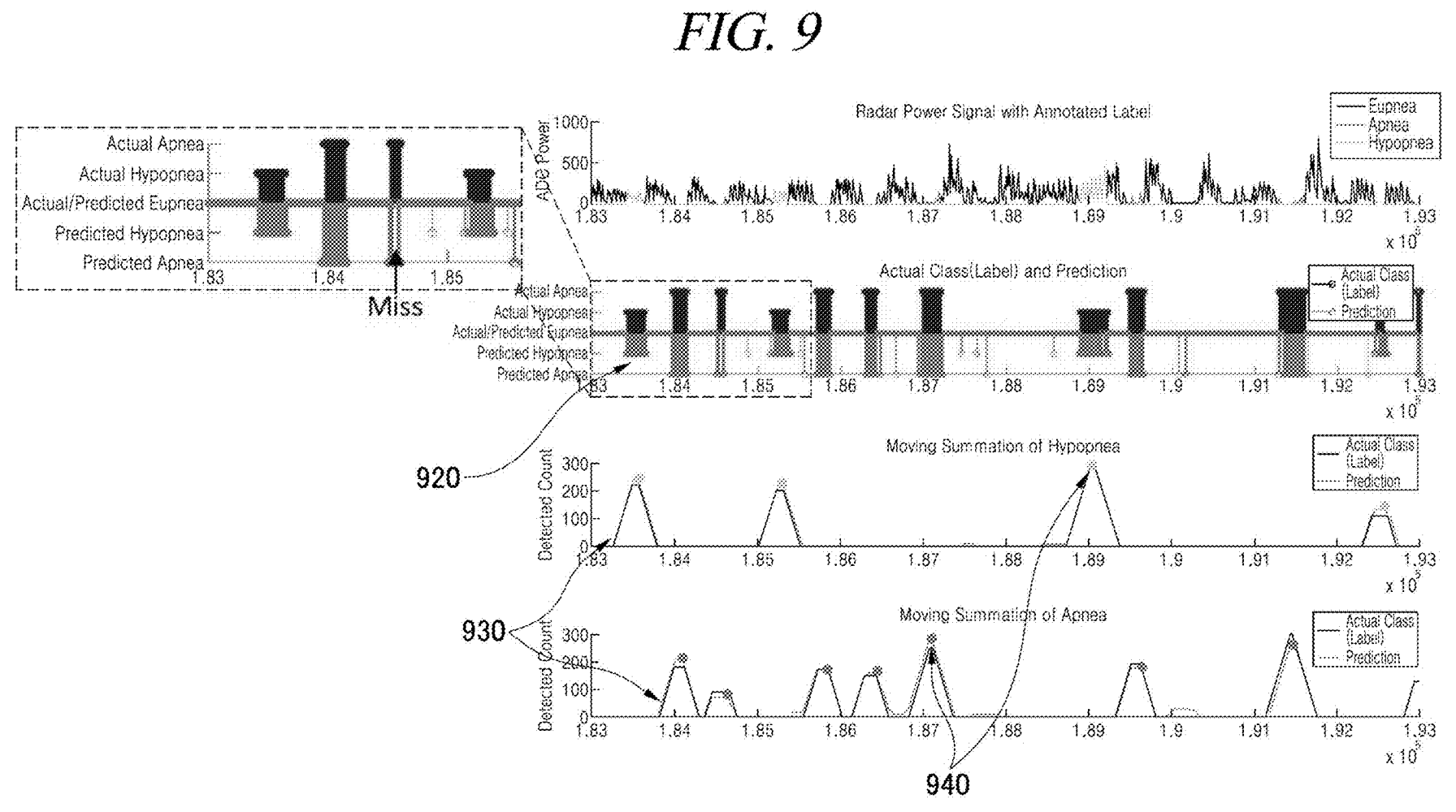

FIG. 9 is a diagram for explaining determining whether a sleep event has occurred. Referring to FIG. 9, the sleep event determination unit 250 may determine that sleep apnea or sleep hypopnea 940 has occurred in the subject based on event occurrence prediction information 930.

Specifically, the prediction information derivation unit 240 may derive an event occurrence prediction value 920 using the prediction model. For example, the prediction information derivation unit 240 may derive the event occurrence prediction value 920 for sleep apnea or sleep hypopnea using the prediction model.

The prediction information derivation unit 240 may calculate a moving summation of the derived event occurrence prediction value 920 for each of sleep apnea or sleep hypopnea. The prediction information derivation unit 240 may generate event occurrence generation information 930 based on the calculated moving summation.

Then, when a maximum likelihood value in the event occurrence generation information 930 is equal to or greater than a predetermined threshold value, the sleep event determination unit 250 may determine that the subject is undergoing the sleep apnea or sleep hypopnea 940.

Also, the sleep event determination unit 250 may detect an occurrence time of the sleep event based on the event occurrence prediction information. For example, the sleep event determination unit 250 may specify the occurrence time of the sleep event as well as the number of occurrences of the sleep event by time-sequentially dividing sleep event occurrences detected from the radar signal received from the subject.

Specifically, the sleep event determination device 100 may independently predict a time-sequentially divided signal, and may improve the accuracy in determination of a sleep event of the subject by using prediction values in similar time domains. That is, the sleep event determination device 100 may independently perform machine learning with a time-sequentially divided signal, and may detect a sleep disorder of the subject by using a maximum likelihood function of a number of prediction values in similar time domains.

Figure 10:
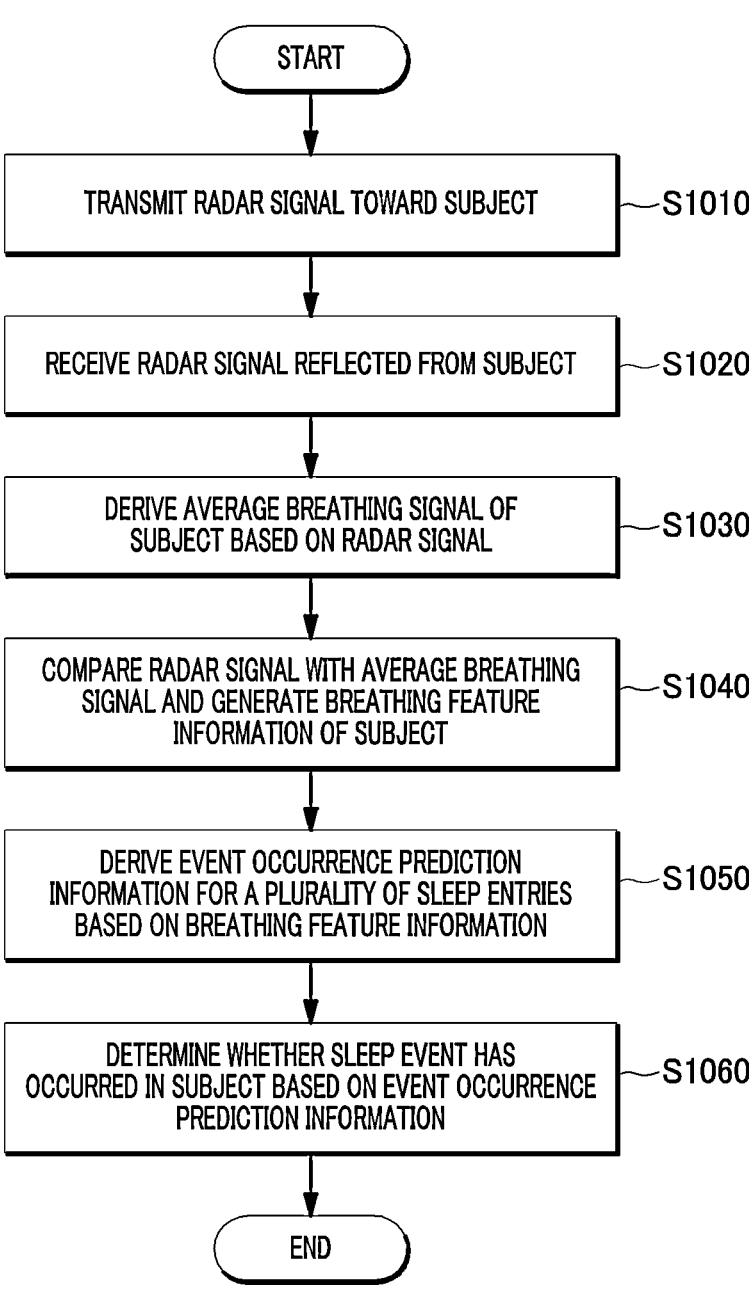
FIG. 10 is a flowchart showing a method for determination of a sleep event.

FIG. 10 is a flowchart showing a method for determination of a sleep event. The method for determination of a sleep event illustrated in FIG. 10 includes the processes time-sequentially performed according to the embodiment illustrated in FIG. 1 to FIG. 9. Therefore, the above descriptions of the processes may also be applied to the method for determination of a sleep event by the sleep event determination device according to the embodiment illustrated in FIG. 1 to FIG. 9, even though they are omitted hereinafter.

In a process 51010, the sleep event determination device may transmit a radar signal toward a subject.

In a process 51020, the sleep event determination device may receive the radar signal reflected from the subject.

In a process 51030, the sleep event determination device may derive an average breathing signal of the subject based on the radar signal.

In a process 51040, the sleep event determination device may compare the radar signal with the average breathing signal and generate breathing feature information of the subject.

In a process 51050, the sleep event determination device may derive event occurrence prediction information for a plurality of sleep items based on the breathing feature information.

In a process 51050, the sleep event determination device may determine whether a sleep event has occurred in the subject based on the event occurrence prediction information.

In the descriptions above, the processes 51010 to 51060 may be divided into additional processes or combined into fewer processes depending on an embodiment. In addition, some of the processes may be omitted and the sequence of the processes may be changed if necessary.

The method for determining disease using a radar in a sleep event determination device described above with reference to FIG. 1 to FIG. 10 can be implemented in a computer program stored in a medium to be executed by a computer or a storage medium including instructions codes executable by a computer. Also, the method for determining disease using a radar in a sleep breath analysis device described above with reference to FIG. 1 to FIG. 10 can be implemented in a computer program stored in a medium to be executed by a computer.

A computer-readable medium can be any usable medium which can be accessed by the computer and includes all volatile/non-volatile and removable/non-removable media. Further, the computer-readable medium may include all computer storage and communication media. The computer storage medium includes all volatile/non-volatile and removable/non-removable media embodied by a certain method or technology for storing information such as computer-readable instruction code, a data structure, a program module or other data. The communication medium typically includes the computer-readable instruction code, the data structure, the program module, or other data of a modulated data signal such as a carrier wave, or other transmission mechanism, and includes a certain information transmission medium.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

I claim:

1. A device for determination of a sleep event using a radar, comprising:
   a transceiver configured to transmit a radar signal toward a subject and receive the radar signal reflected from the subject;
   an average breathing signal derivation unit configured to derive an average breathing signal of the subject based on the radar signal;
   a breathing feature information generation unit configured to:
   derive a breathing feature session by detecting a duration in which the radar signal strays from the average breathing signal for a predetermined threshold time period or more; and
   derive a peak of the radar signal in the detected breathing feature session and generate breathing feature information of the subject based on the derived peak, the average breathing signal, and a predetermined threshold condition;
   a prediction information derivation unit configured to derive event occurrence prediction information for a plurality of sleep items based on the breathing feature information; and
   a sleep event determination unit configured to determine whether a sleep event has occurred in the subject based on the event occurrence prediction information.

2. The device for determination of a sleep event of claim 1,
   wherein the average breathing signal derivation unit is further configured to derive an average breathing signal of the subject every predetermined unit time based on a time sensitivity factor and an amplitude sensitivity factor of the radar signal.

3. The device for determination of a sleep event of claim 1,
   wherein the prediction information derivation unit includes a training unit configured to train a prediction model based on label values for respective sleep events associated with the plurality of sleep items, and
   the prediction information derivation unit is configured to derive the event occurrence prediction information using the prediction model.

4. The device for determination of a sleep event of claim 1,
   wherein the sleep event determination unit is further configured to:
   calculate a moving summation of the event occurrence prediction information;
   derive a maximum likelihood value of the moving summation; and
   determine whether a sleep event has occurred in the subject based on the maximum likelihood value.

5. The device for determination of a sleep event of claim 4,
   wherein the sleep event determination unit is further configured to determine that sleep apnea or sleep hypopnea has occurred in the subject when the maximum likelihood value is equal to or greater than a predetermined threshold value.

6. The device for determination of a sleep event of claim 1,
   wherein the sleep event determination unit is further configured to detect an occurrence time of the sleep event based on the event occurrence prediction information.

7. A method for determination of a sleep event using a radar, comprising:
   transmitting a radar signal toward a subject;
   receiving the radar signal reflected from the subject;
   deriving an average breathing signal of the subject based on the radar signal;
   deriving a breathing feature session by detecting a duration in which the radar signal strays from the average breathing signal for a predetermined threshold time period or more;
   deriving a peak of the radar signal within the detected breathing feature session;
   generating breathing feature information based on the derived peak, the average breathing signal, and a predetermined threshold condition;
   deriving event occurrence prediction information for a plurality of sleep items based on the breathing feature information; and
   determining whether a sleep event has occurred in the subject based on the event occurrence prediction information.

8. The method for determination of a sleep event of claim 7,
   wherein in the deriving an average breathing signal,
   an average breathing signal of the subject is derived every predetermined unit time based on a time sensitivity factor and an amplitude sensitivity factor of the radar signal.

9. The method for determination of a sleep event of claim 7,
   wherein the deriving prediction information further includes:

training a prediction model based on label values for respective sleep events associated with the plurality of sleep items; and deriving the event occurrence prediction information using the prediction model.

10. The method for determination of a sleep event of claim 7, wherein the determining whether a sleep event has occurred further includes:

calculating a moving summation of the event occurrence prediction information;

deriving a maximum likelihood value of the moving summation; and determining whether a sleep event has occurred in the subject based on the maximum likelihood value.

11. The method for determination of a sleep event of claim 10, wherein the determining whether a sleep event has occurred further includes:

determining that sleep apnea or sleep hypopnea has occurred in the subject when the maximum likelihood value is equal to or greater than a predetermined threshold value.

12. The method for determination of a sleep event of claim 7, wherein the determining whether a sleep event has occurred further includes:

detecting an occurrence time of the sleep event based on the event occurrence prediction information.

13. A non-transitory computer-readable storage medium that stores a sequence of instructions for determination of a sleep event using a radar, wherein the sequence of instructions, when executed by a computing device, causes a computing device to:

transmit a radar signal toward a subject;

receive the radar signal reflected from the subject;

derive an average breathing signal of the subject based on the radar signal;

derive a breathing feature session by detecting a duration in which the radar signal strays from the average breathing signal for a predetermined threshold time period or more;

derive a peak of the radar signal within the detected breathing feature session:

generate breathing feature information of the subject based on the derived peak, the average breathing signal, and a predetermined threshold condition;

derive event occurrence prediction information for a plurality of sleep items based on the breathing feature information; and determine whether a sleep event has occurred in the subject based on the event occurrence prediction information.

* * * * *